United States Patent [19]

Simon et al.

[11] Patent Number: 5,731,195
[45] Date of Patent: Mar. 24, 1998

[54] ISOLATED NUCLEIC ACID MOLECULE WHICH CODES FOR A 32 KDA PROTEIN HAVING 11-CIS RETINOL DEHYDROGENASE ACTIVITY, AND WHICH ASSOCIATES WITH P63, A PORTION OF A RETINOL BINDING PROTEIN RECEPTOR

[75] Inventors: Andras Simon, Stockholm; Ulf Hellman; Christer Wernstedt, both of Upsala; Ulf Eriksson, Stockholm, all of Sweden

[73] Assignee: Ludwig Institute for Cancer Research, New York, N.Y.

[21] Appl. No.: 375,962

[22] Filed: Jan. 20, 1995

Related U.S. Application Data

[63] Continuation-in-part of Ser. No. 258,418, Jun. 10, 1994, abandoned.
[51] Int. Cl.$^6$ .............................. C12N 15/12; C12N 5/10
[52] U.S. Cl. ................ 435/252.3; 435/69.1; 435/320.1; 536/23.5; 536/24.31
[58] Field of Search ........................... 435/69.1, 252.3, 435/320.1; 536/23.5, 24.31

[56] References Cited

U.S. PATENT DOCUMENTS 5,177,197  1/1993  Kanzaki et al. ................... 435/240.2

OTHER PUBLICATIONS

Båvik et al., J. Biol. Chem., 267: 23035–23042 (1992).
Båvik et al., J. Biol. Chem., 268: 20540–20546 (1993).
Båvik et al., J. Biol. Chem. 266: 14978–14985 (1991).
Suzuki et al., Chimica et Biophysica Acta; 1163: 201–208 (1993).

*Primary Examiner*—John Ulm
*Attorney, Agent, or Firm*—Felfe & Lynch

[57] ABSTRACT

In accordance with this invention, an RPE cell membrane associated protein which has a molecular weight of about 32 kd, as determined by SDS-PAGE, has now been discovered. This protein, referred to an "p32," forms an oligomeric protein complex with the previously characterized p63 protein, a component of the membrane receptor for RBP. A nucleic acid molecule which codes for the p32 protein has also been isolated and sequence analysis shows that the p32 protein belongs to the family of short chain alcohol dehydrogenases, and exhibits 11-cis retinol dehydrogenase activity, the enzyme which catalyzes conversion of 11-cis-retinol into 11-cis retinaldehyde.

10 Claims, 5 Drawing Sheets

```
         1                                                          50
p32      ..........  ..........  ........MW  LPLLLGVLLW  AALWLLRDRQ
BDH      MMLAARLSRP  LSQLPGKALS  VCDRENGTRH  TLLFYPASFS  PDTRRTYTSQ
FABG     ..........  ..........  ..........  ..........  ..........
EDH      ..........  ..........  ..........  ..........  ..........

51                                                         100
p32      CLPASDAFIF  ITGCDSGFGR  LLALRLD...  QRGFRVLASC  L....TP...
BDH      ADAASGKAVL  VTGCDSGFGF  SLAKHLH...  SKGFLVFAGC  LLKEQGD...
FABG     .MNFEGKIAL  VTGASRGIGR  AIAETLA...  ARGGKVIGTA  ....TSE...
EDH      ....ARTVVL  ITGCSSGIGL  HLAVRLASDP  SQSFKMYATL  RDLKTQGRLW 101                                                        150
p32      SGAEDLQRVA  SSRLHTTLLD  VTDPQSIRQA  VKWVETHV..  GEAGLFGLVN
BDH      AGVRELDSLK  SDRLRTIQLN  VCNSEEVEKA  VETVRSGLKD  PEKGMWGLVN
FABG     NGAQAISDYL  GANGKGLMLN  VTDPASIESV  LEKIRAEFGE  VDI....LVN
EDH      EAARALA.CP  PGSLETLQLD  VRDSKSVAAA  RERVTEGRVD  V......LVC 151                                                        200
p32      NAGVAGIIGP  TPWQTREDFQ  RVLNVNTLGP  IGVTLALLPL  LLQAR.GRVI
BDH      NAGIST.FGE  VEFTSMETYK  EVAEVNLWGT  VRTTKSFLPL  LRRAK.GRVV
FABG     NAGI.TRDNL  LMRMKDEEWN  DIIETNLSSV  FRLSKAVMRA  MMKKRHGRII
EDH      NAGL.GLLGP  LEALGEDAVA  SVLDVNVVGT  VRMLQAFLPD  MKRRGSGRVL

201              ▽                                         250
P32      NITSVLGRLA  ANG.GGYCVS  KFGLEAFSDS  LRRDVAPFGV  RVSIVEPGFF
BDH      NISSMLGRMA  NPARSPYCIT  KFGVEAFSDC  LRYEMHPLGV  KVSVVEPGNF
FABG     TIGSVVGTMG  NGGQANYAAA  KAGLIGFSKS  LAREVASRGI  TVNVVAPGFI
EDH      VTGSVGGLMG  LPFNDVYCAS  KFALEGLCES  LAVLLLPFGV  HLSLIECGPV 251                                                        300
p32      ..RT..PV..  TNLETLEDTL  QACWARL...  ..........  PPATQALYGE
BDH      IAAT..SL..  YSPERIQAIA  KKMWDEL...  ..........  PEVVRKDYGK
FABG     ETDMTRAL..  SDDQRAGILA  QVPAGRL...  ..........  GGAQEIANAV
EDH      HTAFMEKVLG  SPEEVLDRTD  IHTFHRFYQY  LAHSKQVFRE  AAQNPEEVAE

301                                                        350
p32      AFLTKYLRVQ  QRIMNMICDP  DLAKVSRCLE  HALTARHPRT  RYSPGWDAKL
BDH      KYFDEKIAKM  ETYCN.SGST  DTSSVINAVT  HALTAATPYT  RYHPMDYYWW
FABG     AFLASDEAAY  ITGETLHVNG  GMYMV.....  ..........  ..........
EDH      VFLTALRAPK  PTLRYFTTER  FLPLLRMRLD  DPSGSNYVTA  MHREVFGDVP 351                         389
P32      LWLPA.SYLP  ARLVDAVLAW  VLPKPAQTVY  ..........
BDH      LRMQVMTHFP  GAISDKIYIH  ..........  ..........
FABG     ..........  ..........  ..........  ..........
FDH      AKAEAGAEAG  GGAGPGAEDE  AGRSAVGDPE  LGDPPAAPQ
```

ISOLATED NUCLEIC ACID MOLECULE WHICH CODES FOR A 32 KDA PROTEIN HAVING 11-CIS RETINOL DEHYDROGENASE ACTIVITY, AND WHICH ASSOCIATES WITH P63, A PORTION OF A RETINOL BINDING PROTEIN RECEPTOR

RELATED APPLICATION

This application is a continuation-in-part of application Ser. No. 08/258,418 filed Jun. 10, 1994, now abandoned, incorporated by reference.

FIELD OF THE INVENTION

This invention relates to a protein having 11-cis retinol dehydrogenase activity, and which forms a complex with a specific portion of a membrane receptor for plasma retinol-binding protein (RBP) expressed in retinal pigment epithelium (RPE), and more specifically a 32 kDa protein having 11-cis retinol dehydrogenase activity, and which forms a complex with a 63 kDa RBP-binding membrane protein. The invention also involves isolation of the 32 kDa protein (p32), as well as nucleic acid molecules coding for p32 or complimentary to coding sequences therefor, in addition to various applications of these materials.

BACKGROUND OF THE INVENTION

Retinoids (vitamin A-derivatives) have important physiological functions in a variety of biological processes. During embryonic growth and development, as well as during growth and differentiation of adult organisms, retinoids act as hormones and participate in the regulation of gene expression in a number of cell types. See Lied et al. Trends Genet., 17:427–433 (1992). It is believed that these effects are mediated through two classes of nuclear ligand-controlled transcription factors, the retinoic acid receptors (RARs) and the retinoid X receptors (RXRs). Benbrook et al., Nature, 333:669–672 (1988); Brand et al., Nature, 332:850–853 (1988); Giguere et al., Nature, 330:624–629 (1987); Mangelsdorf et al., Nature, 345:224–229 (1990); Mangelsdorf, et al. Genes Dev. 6:329–344 (1992); Petkovich et al. Nature 330:440–450 (1987); and Zelent et al., Nature 339:714–717 (1989).

Apart from their function as hormones in cellular growth and differentiation, retinoids are also involved in the visual process as the stereo isomer 11-cis retinaldehyde of retinaldehyde is the chromophore of the visual pigments. See, e.g. Bridges, *The Retinoids*, Vol. 2, pp 125–176, Academic Press, Orlando, Fla., (1984).

Under normal physiological conditions most cells, both ocular and non-ocular, obtain all-trans retinol as their major source of retinoids. Despite the many different metabolic events taking place in different tissues, it is known that a common extracellular transport machinery for retinol has evolved. Specifically, in plasma, retinol is transported by plasma retinol binding protein (RBP). See Goodman et al., *The Retinoids*, Academic Press, Orlando Fla., Volume 2, pp. 41–88 (1984). The active derivatives of retinol, retinoic acid in non-ocular tissues and mostly 11-cis retinaldehyde for ocular tissues, are then generated by cellular conversion using specific mechanisms. To date, none of these mechanisms have been fully defined at the molecular level and several of the enzymes involved have only been identified by enzymatic activities. See Lion et al., Biochem. Biophys. Acta. 384:283–292 (1975); Zimmermann et al., Exp. Eye Res. 21:325–332 (1975); Zimmermann, Exp. Eye Res. 23:159–164 (1976) and Posch et al., Biochemistry 30:6224–6230 (1991).

Polarized retinal pigment epithelial cells (RPE) are unique with regard to retinoid uptake since all-trans retinol enters these cells via two different mechanisms. Retinol accumulated from RBP is taken up through the basolateral plasma membrane, while all-trans retinol, presumably taken up from the interstitial retinol-binding protein (IRBP) following bleaching of the visual pigments, may enter through the apical plasma membrane. See Bok et al., Exp. Eye Res. 22:395–402 (1976); Alder et al., Biochem. Biophys. Res. Commun. 108:1601–1608 (1982); Lai et al., Nature 298:848–849 (1982); and Inu et al., Vision Res. 22:1457–1468 (1982).

The transfer of retinol from RBP to cells is not fully understood. In a number of cell types, including RPE, specific membrane receptors for RBP have been identified, which is consistent with a receptor-mediated uptake mechanism for retinol. For example, there are disclosed isolated retinol binding protein receptors, nucleic acid molecule coding for these receptors and antibodies binding to the receptor. These teachings relate to the first of the two mechanisms. See Bavik et al., J. Biol. Chem. 266:14978–14985 (1991); Bavik, et al. J. Biol. Chem. 267:23035–23042 1992; Bavik et al., J. Biol. Chem. 267:20540–20546 (1993); and copending U.S. application Ser. No. 083,539 and International Publication WO 93/23538, all of which are incorporated by reference herein. See also Heller, J. Biol. Chem. 250:3613–3619 (1975); and Bok et al., Exp. Eye Res. 22:395–402 (1976).

Retinol uptake on the apical side of the RPE for the regeneration of 11-cis retinaldehyde is less well characterized. However, regardless of the origin of all-trans retinol, the synthesis and apical secretion of 11-cis retinaldehyde seems to be the major pathway for accumulated retinol in the RPE. At present, it is not known whether similar mechanisms are used with regard to cellular retinol uptake through the basolateral and the apical plasma membranes. However, available data show that functional receptors for RBP are exclusively expressed on the basolateral plasma membrane of RPE-cells. Bok et al., Exp. Eye Res. 22:395–402 (1976).

It is also known that retinal pigment epithelial cells (RPE) express a 63 kDa protein (p63). It has also been shown by chemical cross-linking that this protein may be part of an oligomeric protein complex which functions as a membrane receptor for plasma retinol-binding protein (RBP) in RPE-cells, or a component of the retinoid uptake machinery in RPE cells. See Bavik et al, *J. Biol. Chem.* 266:14978–14875 (1991); Bavik et al., *J. Biol. Chem.* 267:23035–23042 (1992), and U.S. application Ser. No. 083,539 and PCT application WO93/23538. The p63 protein has been isolated and the corresponding cDNA cloned. See Bavik et al., J. Biol. Chem. 267:20540–20546 (1993). However, there is nothing in these references suggesting the existence of the protein which is a feature of this invention.

SUMMARY OF THE INVENTION

In accordance with this invention, an RPE cell membrane associated protein which has a molecular weight of about 32kd, as determined by SDS-PAGE, has now been discovered. This protein, referred to as "p32," forms an oligomeric protein complex with the previously characterized p63 protein, a component of the membrane receptor for RBP. A nucleic acid molecule which codes for the p32 protein, has also been isolated and sequence analysis shows that the p32 protein belongs to the family of short chain alcohol dehydrogenases, and exhibits 11-cis retinol dehydrogenase activity, the enzyme which catalyzes the stereospecific conversion of 11-cis-retinol into 11-cis retinaldehyde in the presence of cofactor NAD+.

As will be shown, p32 has many important uses. For example, owing to its membrane bound 11-cis-retinol dehydrogenase activity, which catalyzes the conversion of 11-cis-retinol to 11-cis-retinaldehyde, a major metabolic step in retinoid metabolism in RPE-cells, retinoid accumulation and metabolism which may lead to retinitis pigmentosa, may be directly or indirectly tied to the presence of p32, and/or its activation or inhibition. As p32 has also been found to be a member of the short chain alcohol dehydrogenase super family, many known alcohol dehydrogenase inhibitors (and activators) are available to develop activity assays, and thus diagnostic materials for retinol uptake, and ocular retinoid metabolism.

These and other aspects of this invention are more fully discussed in the following Detailed Discussion with accompanying drawings.

BRIEF DESCRIPTION OF THE DRAWINGS

FIG. 3 illustrates amino acid sequence alignments of p32 and some related proteins belonging to the family of short-chain alcohol dehydrogenases. The sequences of these proteins are set forth in SEQ ID NO:11 (rat D-b hydroxybutyrate dehydrogenase), SEQ ID NO:12 (human estradiol 17-b dehydrogenase (hEDH)), SEQ ID NO:13 (*E.coli* 3-exoacyl [acyl carrier protein] reductase (FABg)), and SEQ ID NO:14 (p32).

DETAILED DISCUSSION OF PREFERRED EMBODIMENTS

It is known that plasma retinol binding protein (RBP) can be chemically cross-linked to a high molecular weight complex of a 63 kDa protein (p63) receptor of retinal pigment epithelium membranes (RPE), forming an RBP-RBP receptor complex with elution properties of globular proteins of similar sizes having apparent molecular weights of approximately $M_r$ 150,000 and 450,000. See Bavik et al, J. Biol. Chem. 266:14978–14875 (1991), and Bavik et al., J. Biol. Chem. 267:23035–23042 (1992). The protein responsible for binding of RBP, which expression is restricted to RPE, has been identified as a 63 kDa protein (p63). Through the generation of a monoclonal antibody A52 (mAb A52) to the 63 kDa protein which binds the RBP-RBP receptor complex and p63, and immunoaffinity chromatographic analysis, a majority of p63 is eluted as a monomer, with a significant portion of the protein found in positions corresponding to higher molecular weight species. This indicates that p63 exists in an oligomeric protein complex with other protein components. Bavik et al., J. Biol. Chem. 266:14978–14985 (1991), and Bavik et al, J. Biol. Chem. 267:23035–23042 (1992). Therefore, the following procedure was carried out to investigate the molecular characteristics of such oligomeric protein complexes, and whether p63 forms a complex with other proteins specific to RPE. The results show that a 32 kDa membrane associated protein (p32) indeed forms a complex with p63.

EXAMPLE 1

Bovine RPE-cells were isolated and membrane fractions were prepared as described in Bavik et al, J. Biol. Chem. 266:14978–14875 (1991). RPE-membrane proteins were then solubilized in phosphate-buffered saline (PBS)(20 mM sodium phosphate, ph 7.2, containing 150 mM NaCl), containing 1% 3-[(3-cholamido-propyl)dimethylammonio]-1-propane sulfonic acid (CHAPS) at 1 mg of total membrane protein/ml of buffer. Remaining material was removed by ultracentrifugation at 100,000×g for 1 hour. Next, 500 ul aliquots of the solubilized membranes were subjected to gel filtration on a Sepharose 6 column equilibrated in PBS containing 1% CHAPS. The column was operated at a flow rate of 0.2 ml/min and 500 ul fractions collected. Proteins eluted in fractions corresponding to globular proteins of $M_r$ 150,000 to 400,000 were then radiolabelled with $Na^{125}I$ using the well-known Chloramin T procedure. Non-incorporated $^{125}I$ was removed by gel filtration on Sepahadex G-25 packed in a Pasteur pipette.

Aliquots of the radiolabelled proteins were then diluted in PBS containing 1% CHAPS and 1% bovine serum albumin and subsequently subjected to immunoprecipitation using the mAb A52 to p63 (5 ug per incubation) or using two polyclonal rabbit antisera to p63 (3 ul of serum per incubation) See Bavik et al., J. Biol. Chem. 267:23035–23042 (1992). Non-specific immunoprecipitation was monitored in parallel incubations using an unrelated mAb and preimmune rabbit serum. Fifty ul of a 50% slurry of protein A-Sepharose was added to the incubations for 30 minutes. The beads were subsequently carefully washed with PBS containing 1% CHAPS and the eluted material then prepared for SDS-PAGE analysis, which was carried out according to Blobel et al. J. Cell. Bio. 67:835–851 (1975).

Figure 1A:
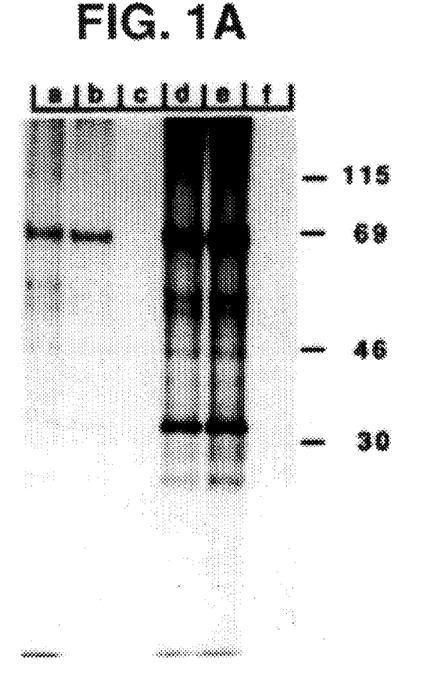
FIG. 1A shows SDS-PAGE analysis of radiolabeled protein from RPE-membranes and immunoprecipatation with mAb A52 against p63.

Referring now to FIG. 1A, autoradiograms of the SDS-PAGE gels showed that both types of reagents reacted with p63, whereas the unrelated mAb or preimmune rabbit serum did not precipitate p63. In all lanes containing immunoprecipitated p63 there was an enrichment of a $M_r$ 32,000 protein. Since both mAb A52 and the rabbit antisera to p63 are highly specific for p63 (See, for example, Bavik et al., J. Biol. Chem. 267:23035–23042 (1992)), it can be concluded that the $M_r$ 32,000 protein (p32) coprecipitated in the aforesaid analysis by binding to p63. The analysis also identified a double band of $M_r$ 50,000–52,000 which precipitated along with p32 and p63 (FIG. 1 d, e).

EXAMPLE 2

Figure 1B:
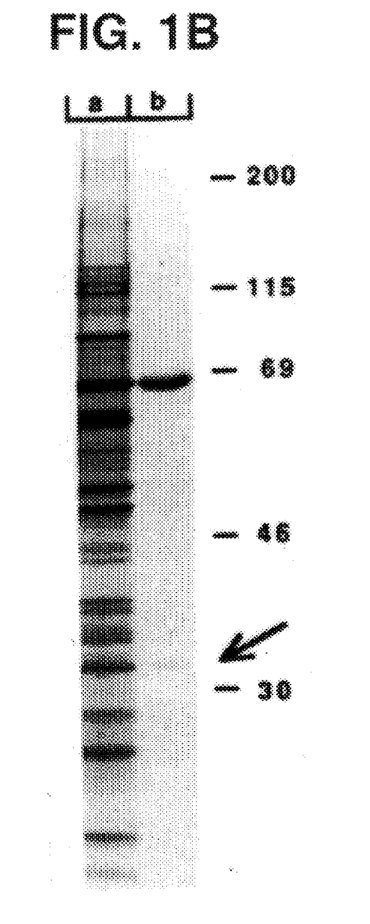
FIG. 1B shows SDS-PAGE analysis of RPE-membrane proteins bound and eluted through an mAb A52 immunoaffinity column, and the presence of p32 in the eluted faction from the immunoaffinity column.

Experiments were then carried out to identify p32. Advantage was taken of the fact that p32 specifically interacts with p63 as shown supra. Thus, detergent solubilized RPE-membrane proteins were passed over an immunoaffinity column containing mAb A52. Referring now to FIG. 1B, lane b, following a washing procedure, bound proteins were eluted at high pH in a CHAPS-containing buffer, and SDS-PAGE analysis and Coomassie staining of the eluted fractions revealed p63 to be specifically retained and eluted from the immunoaffinity column. Further, a weekly stained band corresponding to p32 could be visualized in the eluate from the A52 column. As shown in FIG. 1B, a comparison of the total protein profile of solubilized RPE membranes and the eluted fraction from the A52 column show that the p32 protein is not efficiently retained therein. However, the appearance of p32 in the eluted fraction from the A52 column, but not in the eluted fraction from the column containing an unrelated Ig, indicate a specific interaction of p32 with p63. This result is consistent with previous immunoprecipitation data, and shows that p32 is complexed to p63 and is retained on the immunoaffinity column due to this complex formation.

Having now identified p32 as component of a complex with p63 in RPE-membranes, the p32 protein itself was isolated by SDS-PAGE of eluted fractions of solubilized RPE-membranes from the A52 immunoaffinity column, as set forth below in Example 3.

EXAMPLE 3

RPE-membranes were solubilized in PBS containing 1% CHAPS as set out above and then incubated with mAb A52 Ig coupled to CNBr-activated Sepharose 4B beads (Pharmacia) in a Bio-Rad poly prep column (Bio-Rad) by end-over-end rotation at +4° C. Following a 2 hour incubation, the beads were allowed to settle and the column was quickly washed with 5 column volumes of PBS containing 1% CHAPS. Bound proteins were then eluted with 50 mM triethanolamine buffer (pH 11.2) containing 1% CHAPS. The pH of the eluate was quickly adjusted to 8.0 by the addition of 1M Tris-NCl buffer containing 1% CHAPS. The eluted fractions were subjected to SDS-PAGE, and the separated proteins then visualized by Coomassie Blue staining. A band corresponding to p32 (SDS-PAGE, 32kDa), was found.

To determine the primary structure of p32 partial amino acid sequence analysis of the isolated protein was undertaken by first cutting out a portion of the aforesaid Coomassie stained band corresponding to approximately 2–5 ug of the 32kDa protein, then lyophilizing the gel piece to dryness. The gel was rehydrated in buffer containing modified trypsin and incubated to generate various peptides for extraction and analysis. A preferred procedure is set forth below in Example 4.

EXAMPLE 4

Coomassie stained bands containing the p32 protein from Example 2 were excised and treated according to Rosenfeld et al. Anal. Biochem. 15:173–179 (1992) with minor modifications. The gel pieces were washed twice for 30 min at 30° C. with 100 ul of 0.2M ammonium bicarbonate buffer containing 50% acetonitrile and thereafter completely dried under a stream of nitrogen. The gel pieces were subsequently rehydrated with 5 ul of 0.2M ammonium bicarbonate buffer containing 0.02% Tween 20 and 0.5 ug of modified trypsin. Trypsin was added from a stock solution prepared in 1 mM HCl. Rehydration continued by the addition of 5 ul portions of the 0.2M ammonium bicarbonate buffer until the gel pieces obtained their original sizes. The rehydrated gel pieces were then incubated overnight at 30° C. The protease activity was inhibited by the addition of trifluoroacetic acid (TFA) to a final concentration of 1%. The supernatant was recovered and combined with two extracts made with 150 ul of 0.1% TFA in 60% acetonitrile. The organic phase was reduced and the digest was subjected to HPLC using a reverse phase mRPC C2/C18 SC 2.1/10 column operated in a SMART system. The sample was eluted with a gradient of acetonitrile in 0.065% TFA and fractions containing discrete peptides were collected using the automatic peak fractionation option. Five of the identified peptides were selected for amino acid sequence analysis using an ABI 470A sequencer equipped with a model 120A PTH analyzer (applied Biosystems Inc. Foster City, Calif.). The results are set forth below in Table 1.

TABLE 1

| Amino acid sequences determinations of five peptides isolated from trypsin digested p32. | |
|---|---|
| p321 | L—V—E—A—V—L—A—E—V—L—P—K—P—A—Q—T—V—A  (SEQ ID NO: 1)<br>    (D)*                    (W)                              (Y) |
| p322 | Y—S—P—G—W—D—A—K  (SEQ ID NO: 2) |
| p323 | T—P—V—T—N—L—E—T—L—E—D—T—L—Q—A  (SEQ ID NO: 3) |
| p324 | D—V—A—P—F—G—V  (SEQ ID NO: 4) |
| p325 | L—H—T—T—L—L—D—V—T—D—P—Q—S—I  (SEQ ID NO: 5) |

Protein SEQ ID NOS: 1–5 can be used alone or ligated to hapten by well known methods.
*The amino acid residues given within the parentheses are the residues deduced from the cDNA sequence in the same positions.

Next, to determine the complete primary structure of p32, four degenerative oligonucleotide mixtures, OM1–OM4, as set forth below in Table 2 were synthesized based on the amino acid sequences of the p321 and p323 sequenced peptides of Table 1. The procedure is as follows in Example 5.

EXAMPLE 5

Four degenerate oligonucleotide mixtures derived from peptides p321 and p323 were synthesized using well-known techniques. The two sense mixtures (OM1 and OM3) were derived from the N-terminal amino acids 1–5 of p321 and 2–6 of p323. The antisense mixtures (OM2 and OM4) were derived from amino acids 12–17 of p321 and 10–15 of p323. All nucleotide mixtures were synthesized with a 4 bp 5' extension and an Eco RI-site for subsequent cloning of the PCR products. The sequences of the oligonucleotide mixtures are set out below in Table 2, and the Eco RI-site is underlined. Positions containing all four bases are marked N.

Table 2

OM1: ACGT GAA TTC TN GTN GA (A.G)GCN GT (SEQ ID NO:6)
OM2: ACGT GAA TTC AC NGT (T.C)TG NGC NGG(T.C)TT (SEQ ID NO: 7)
OM3: ACGT GAA TTC CCN GTN ACN AA(T.C)(C.T)T (SEQ ID NO: 8)
OM4: ACGT GAA TTC GC(T.C)TG NA(A.G)NGT(A.G) TC(T.C)TC (SEQ ID NO: 9)

Single stranded "complementary" cDNA from reverse transcribed RPE mRNA and four combinations of the above-described degenerate nucleotide mixtures were employed in polymerase chain reactions (PCR) using a standard procedure. Following the amplification procedure, aliquots of the PCR reaction products were analyzed by agarose gel electrophoresis. The procedure is set out below in Example 6.

EXAMPLE 6

To carry out the PCR amplifications, first strand cDNA was synthesized by standard procedures using avian myelostosis virus reverse transcriptase. Twenty ug of total RNA from isolated RPE-cells were used and the reaction was primed with oligo (dT) 15. Aliquots corresponding to 2 ug of total RNA was used in each subsequent PCR reaction. The PCR reactions were performed using a final concentration of 0.5 uM of the oligonucleotide mixtures in a 100 ul reaction. Taq polymerase was used. Following 30 cycles (2 minute at 95° C., 1 minute at 55° C. and 2 minute at 72° C.), aliquots of the reactions were analyzed on 4% GTG agarose gel containing 5 ug/ml of ethidium bromide.

Figure 2:
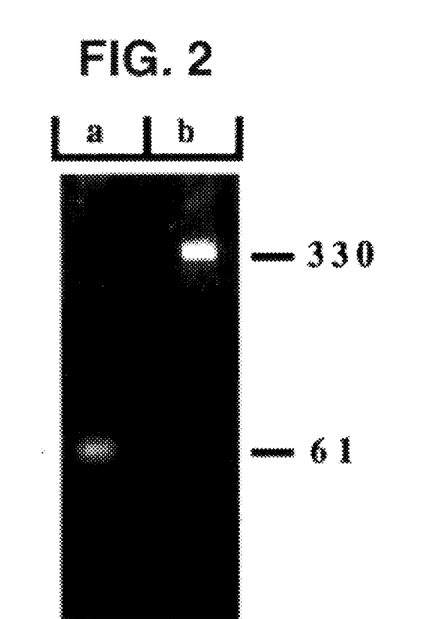
FIG. 2, in panel a, shows visualization on an agarose gel of a 61 bp PCR-amplified fragment using oligonucleotide mixtures OM1 and OM3, both derived from peptide 321, deduced from partial amino acid sequence determination of trypsin digested p32. Panel b shows visualization of a 330 bp-PCR amplified fragment using oligo-nucleotide mixtures OM2 and OM3, derived from peptides p323 and p321, respectively, as deduced from partial amino acid sequence determination of trypsin digested p32.

As shown in FIG. 2A, amplifications using the oligonucleotide mixtures OM1 and OM2, both derived from peptide p321, resulted in an amplified 61 bp fragment. Amplifications using mixtures OM3–OM4 and OM1–OM4 failed to yield any products. Finally, as shown in FIG. 2B, amplification using OM3–OM2 resulted in an amplified 330 bp fragment.

Subsequent sequence analysis of the 61 bp and 330 bp fragments confirmed that cDNA sequences have been amplified which corresponded to the peptide sequences generated in the previous amino acid sequence analysis. Differences between the deduced amino acid sequences from amplified PCR fragments and the generated amino acid sequence of peptide p321 indicates the generation of specific probes suitable for the isolation of full length cDNA clones encoding p32.

To isolate a full length cDNA clone, an RPE-specific lambda ZAP-II cDNA library was screened with the 330 bp fragment as the probe. Five independent lambda clones were isolated from approximately 200,000 clones, and subcloned by in vivo excision. The cDNA clone pλ321 contained the longest insert, (approximately 1.1 Kb), and was selected for use in further studies.

Both strands of pλ321 were fully sequenced with the insert being 1104 bp long, excluding linkers used to prepare the cDNA library. The procedure is set out below in Example 7.

EXAMPLE 7

The amplified products using OM1–OM2 (61 bp) and OM3–OM2 (330 bp) were digested with EcoR1, gel purified and cloned into EcoR1-cut vector pBS. The 32p-labelled 330 bp fragment was used to screen a RPE-specific λZAP II cDNA library as previously described. Bavik et al., J. Biol. Chem. 267:20540–20546 (1993), incorporated by reference. Five positive λ clones were isolated and the inserts were subcloned in pBluescript by in vivo excision following the manufacturers instructions. Clone pλ321 contained an insert of 1.1 Kb, and both strands were fully sequenced using Sequenase with T3, T7 or M13 universal primers or with internal primers.

The nucleotide sequence of pλ321 and the predicted amino acid sequence of p32 are shown in (SEQ ID NO:10). Nucleotides are numbered on the left and amino acid residues on the right. Amino acid 1 is initial methionine ("Met").

As shown in FIG. 3, the 1.1 kbp insert contains one long open reading frame encoding 318 amino acid residues with a calculated mass of 35.041D. The first methionine residue lies in a good context according to the Kozak rules for transcription initiation and is likely to be the initiation codon. See Kozak, Cell, 44:283–292 (1986). This inference is strengthened by the fact that in vitro translation of synthetic mRNA transcribed from pλ321 gives rise to a $M_r$ 32,000 protein (SDS-PAGE analysis), as set out below, but there is no stop codon in frame in the upstream 35 bp 5'-untranslated region of the cDNA. As also shown in SEQ ID NO:10, the 100 bp 3'-untranslated region ends with a putative polyA-tract, and a polyA-signal was identified in the upstream sequence (bp 1104–1110).

The deduced amino acid of pλ321 and the amino acid sequences of the five generated tryptic peptides (Table 1) differ in only 3 positions out of the 62 residues available for a comparison. All 3 differences are found in the peptide p321 but the nucleotide sequence in this region of a second cDNA clone (pλ324) is identical to that of pλ321. This indicates that the amino acid sequence determination of peptide p321 was probably incorrect although it cannot be excluded that the differences are due to the presence of different alleles of p32. These data demonstrate that pλ321 contains the complete coding region of p32.

Again, referring to SEQ ID NO:10, a consensus sites for N-linked glycosylation (amino acid residues N-I-T) could be found in the deduced amino acid sequence at position 160–162.

Additionally, it has been found that p32 shows sequence similarities to short-chain alcohol dehydrogenases. Referring now to FIG. 3 a search through the Swissprot protein data base revealed that p32 is structurally related to several previously sequenced proteins. It is most closely related to a mitochondrial matrix dehydrogenase, the D-β-hydroxybutyrate dehydrogenase (BDH) Churchill et al; Biochem. 31:3793–3799 (1992) and shows less but significant similarities to two other proteins, the 3-oxoacyl[acyl carrier protein] reductase from E. coli (Rawlings et al., J. Biol. Chem. 267–5751–5754 (1992)) and the human estradiol 17 β-dehydrogenase (Peltoketo et al., FEBS Lett., 239:73–77 (1988) and Leu et al., Mol. Endocrinol. 3:1301–1309 (1989) ). All the related proteins fall into the protein super-family of short-alcohol dehydrogenases. This protein superfamily comprises approximately 50 different proteins (Persson et al. Eur. J. Biochem, 200:537–593 (1991)). The overall sequence homology between p32 and BDH is around 39%. The level of homology to the E. coli reductase and to the estradiol 17-β-dehydrogenase is lower (31% and 33% respectively)

Optimal multiple alignment identified several conserved regions shared by p32 and the most closely related proteins (boxed areas in FIG. 3). The first region involving residues 63–69 (using the numbering in FIG. 3) which displayed the conserved motif G-X-X-X-G-X-G is believed to be the binding site for cofactors NAD, NADP or its reduced forms. Another conserved region is found between residues 148–153 (consensus sequence L-V-N-N-A-G) but no functional characteristics have yet been attributed to that sequence motif. The sequence motif Y-X-X-X-K, thought to be the active site, is the most highly conserved motif in short-chain alcohol dehydrogenases and is present in p32 residues 175–179 See Persson et al., Eur. J. Biochem. 200:537–593 (1991). These similarities demonstrate that p32 exhibits several features of a functional short-chain alcohol dehydrogenase.

Figure 4:
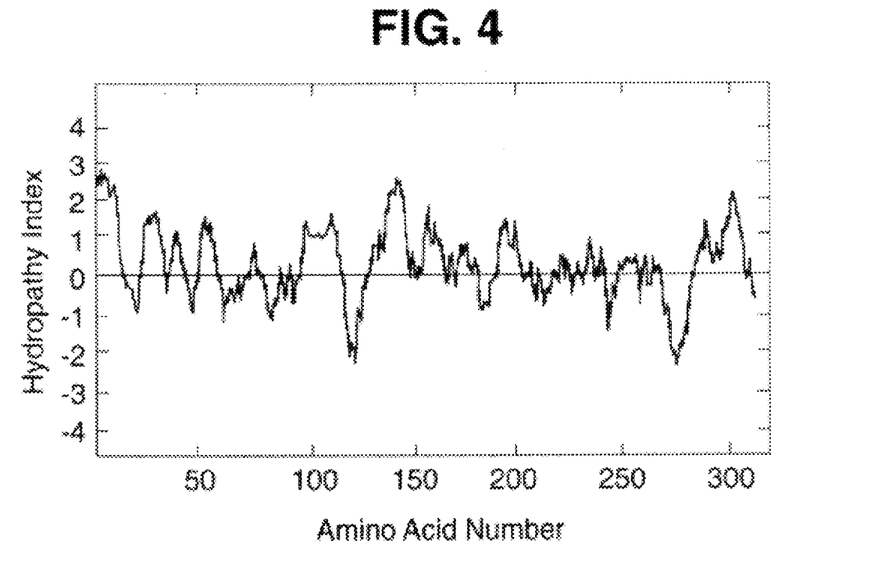
FIG. 4 illustrates analysis of the amino acid sequence of p32.

As shown in FIG. 4, hydropathy analysis of the amino acid sequence of p32 reveals several hydrophobic stretches, indicating that p32 is a membrane-associated protein. The first 18 amino acids are hydrophobic, and this region has characteristics of a classical signal sequence. However, a consensus site for signal peptidase cleavage could not be identified. See Von Heijne, Nucl. Acid Res., 14:4683–4690 (1986). The region between residues 130 to 150 are hydrophobic and there is a relatively long hydrophobic stretch near the C-terminus of the protein. Thus, p32 displays several hydrophobic regions which are potential membrane spanning segments. In light of the homology to the family of short-chain alcohol dehydrogenases as shown above, it is likely that the central hydrophobic region of p32 (residues 130–150) is not used as a membrane anchor. Instead, both the N-terminal and the C-terminal regions are potential membrane anchoring domains.

To determine the mode of interaction of p32 with membranes, p32 was synthesized by in vitro translation using a reticulocyte lysate system with mRNA transcribed from linearized pλ321. The procedure is set out in Example 8 below:

EXAMPLE 8
Expression of p32 by in vitro translation

In vitro transcribed mRNA encoding p32 was synthesized from linearized Pλ321 using T7 RNA polymerase. In vitro translation reactions were carried out using nuclease treated rabbit reticulocyte lysate following the manufacturer's instructions. Fifty ng of mRNA was included in each reaction, with or without the addition of dog pancreatic microsomes. To isolate membrane inserted p32, the microsomes were collected by centrifugation at 12,000×g for 10 min at 4° C. The microsomes were carefully resuspended in PBS and recentrifugated.

Figure 5:
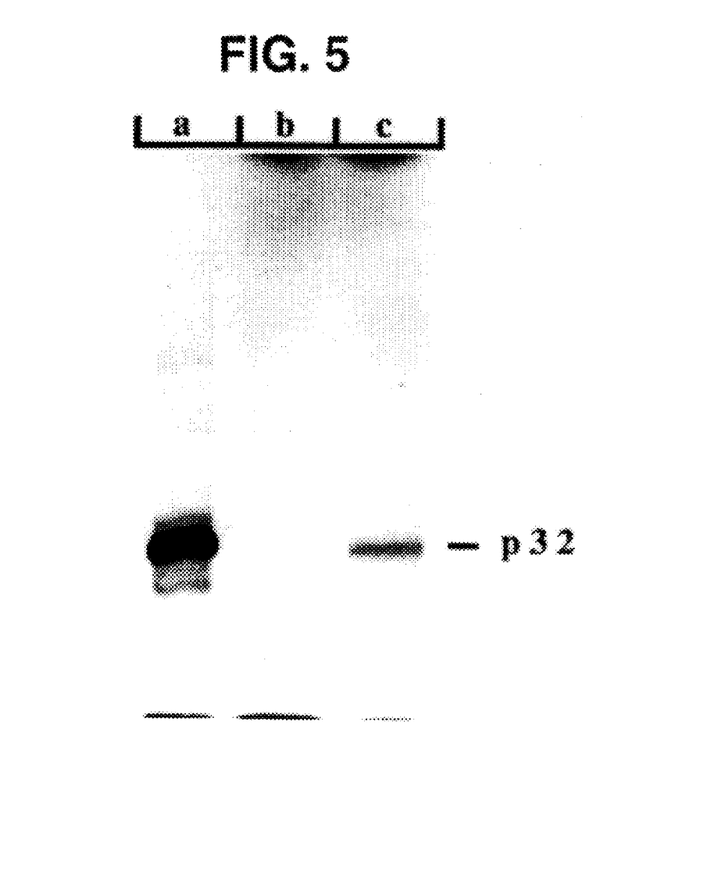
FIG. 5 panels a, b and c, inclusive illustrate membrane interaction of p32 synthesized in vitro.
Figure 6:
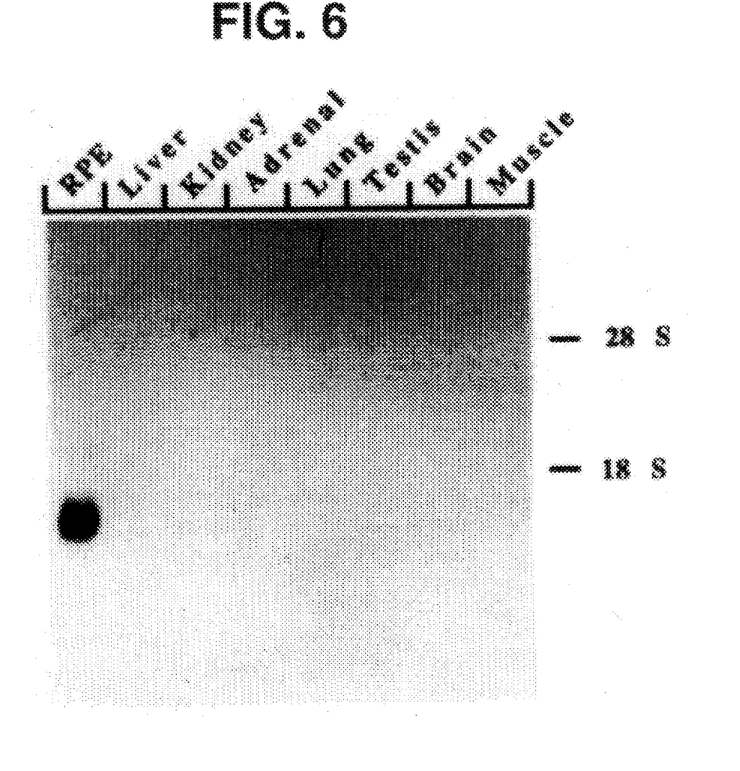
FIG. 6 illustrates the restricted expression of transcripts corresponding to p32.

As shown in FIG. 5, translation in the presence of dog pancreatic microsomes showed that p32 becomes almost quantitatively membrane associated and migrates as a $M_r$ 32,000 species in SDS-PAGE. Translation in the absence of acceptor membranes similarly yields a $M_r$ 32,000 protein. These data indicate that the N-terminal hydrophobic sequence acts as a signal sequence but it is not removed by the signal peptidase, and such supports the previous observation that a consensus site for signal peptidase cleavage could not be identified in the deduced primary sequence.

The tissue expression of p32 was analyzed by Northern blotting analyses using total RNA isolated from bovine RPE, liver, kidney, adrenal, lung, testis, brain and muscle. The procedure is set out in Example 9.

EXAMPLE 9

Northern blot analyses

Twenty ug of total RNA isolated from a number of tissues was electrophoresed on a 1% agarose under denaturing conditions and transferred to a Hybond-N nylon filter. The filter was hybridized with 32P-labelled full length cDNA encoding p32 under stringent conditions. The details of the isolation of total RNA, hybridization conditions and washing procedure were identical to those previously described in Bavik, et al., J. Biol. Chem. 267:20540–20546 (1993).

Hybridization at high stringency with the 1.1 Kb insert of pλ321 as the probe, revealed abundant expression of transcripts corresponding to p32 only in RPE but not at a detectable level in several other tissues. The size of the major transcript was 1.4 kb but other less abundant transcripts could be visualized after prolonged exposure of the filters both in RPE as well as in other tissues.

Thus, as shown above, this invention provides a method for the isolation and characterization of a novel protein, p32, which associates with the p63 of RPE. The primary structure of p32 demonstrates that it has all the critical features of a functional short-chain alcohol dehydrogenase including a putative cofactor binding site and essential residues involved in the catalytic mechanism, namely the almost invariant tyrosine containing sequence motif Y-X-X-X-K (Persson et al., Eur. J. Biochem. 200:537–543 (1991)). The restricted tissue expression and the abundance of p32 in RPE indicates that this protein carries out a function which is unique to the RPE. This possibility, and the fact that it forms a complex with p63 which previously has been shown to be a component of the retinoid uptake machinery in RPE-cells (Bavik, et al., J. Biol. Chem. 267:23035–23042 (1992)), shows that the substrate for p32 is a retinoid.

A major metabolic step in retinoid metabolism in RPE-cells is the conversion of 11-cis retinol to 11-cis retinaldehyde. Based on the results obtained hereinabove showing the restricted expression of p32 in the RPE, and the particular biochemical properties of this protein further investigation confirmed that p32 is in fact an 11-cis-retinol dehydrogenase, the enzyme which catalyzes this reaction.

EXAMPLE 10

Expression of p32 in COS-cells and enzymatic analysis of the properties of recombinant p32.

p32 was first expressed in COS-cells using a eukaryotic expression vector, and then microsome fractions from transfected cells and control cells were subjected to immunoblotting analysis to verify the expression of p32 at the desired levels, as follows:

Specifically, the EcoR1—insert of pλ321 was cloned into the EcoR1-digested eucaryotic expression vector pSG5. See Green et al., Nucl. Acid Res. 16:39 (1988). COS-cells were maintained in Dulbecco's minimal essential medium supplemented with 10% fetal bovine serum, 2 mM glutamine and antibiotics. The cells were seeded into 60 mm petri dishes ($4\times10^5$ cells per dish) and transfected with 5 ug of plasmid per dish using DEAE dextran. Control cells were transfected with equal amounts of the parental vector alone. After treatment with 10% DMSO for 2 minutes, the cells were incubated for 72–96 hours, and then harvested by scraping the dishes with a rubber policeman, and the cells thereafter collected by low speed centrifugation. The collected cell pellets were next resuspended in hypotonic buffer (10 mM Tris-HCl, pH 7.5 containing 1 mM phenyl-methylsufonyl fluoride), put on ice for 20 minutes, and then homogenized using a Dounce homogenator. Unbroken cells and debris were removed by centrifugation (3000×g)for 15 minutes. Microsomes were subsequently collected by ultracentrifugation at 100,000×g for 1 hour; membrane pellets were stored at −80° C. until further analyzed.

Antisera to p32 were generated by injecting rabbits with p32 (amino acid residues 19–318) expressed as a fusion protein with GST. The bacterial expression vector pGEX 2T was used and induction and purification of the GST-fusion protein was, as recommended by the supplier (Pharmacia). Each rabbit received a subcutaneous injection of 75 ug of fusion protein emulsified in Freunds complete adjuvant. The rabbits were boostered with 50 ug of fusion protein emulsified in Freunds incomplete adjuvant every second week. Blood was collected every second week. The immune rabbit sera were passed over a column containing GST fusion-protein immobilized on CNBr activated Sepharose beads. Bound Ig was eluted with 0.1M sodium citrate buffer (pH 3.0), containing 0.5M NaCl. To remove Ig to the GST portion of the fusion protein, the eluted Ig was similarly incubated with GST-coupled Sepharose beads and the unbound Ig fraction was used. For immunoblot analysis of the over expressed protein, the Ig was used at a concentration of 1 ug per ml. The details of the immunoblotting procedure are described in detail in Bavik et al., J. Biol. Chem., 267:23035–23042 (1992) the disclosure of which is herein incorporated by reference.

Figure 7A:
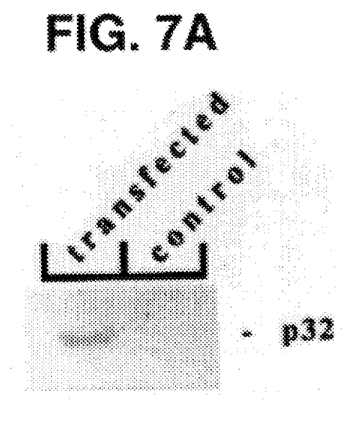
FIG. 7A illustrates expression of p32 in transfected cells for further enzymatic activity analysis of 11-cis retinol dehydrogenase activity.

AS shown in FIG. 7A, the above procedure resulted in expression of p32 in cells transfected with the recombinant expression vector, but not in control cells that were mock transfected.

Next, the enzymatic properties of p32 expressed in COS-cells was assayed in a manner similar to that as described in the study of 11-cis-retinol dehydrogenase activity in microsomal fractions of RPE cells. See Saari et al., Anal. Biochem 213:28–13226 (1993).

In particular, the enzymatic activity of p32 was confirmed by incubating the microsomal fractions from the aforementioned transfected cells, and from control cells lacking p32, with varying combinations of the different stereo isomeric substrates, i.e., 11-cis-retinol or all-trans-retinol, in the presence of either cofactor NAD+ or NADP.

To prepare the substrate, 11-cis retinol was synthesized from 11-cis-retinaldehyde using sodium borohydride, as set fourth in Heller et al., J. Biol. Chem. 248:6308–6316 (1973), and stored under argon at 80° C. HPLC analysis confirmed the quantitative reduction of 11-cis-retinaldehyde to 11-cis-retinol, and all manipulations with the retinoids were done under subdued lighting conditions.

To assay for p32 activity in transfected cells, the final concentration of 11-cis-retinol and all-trans-retinol (obtained from Sigma Chemical Co.) in the incubations was reduced to 100 uM. Twenty ug of total membrane protein from COS-cells expressing p32 or from control cells were used in each incubation, and thereafter a 30 minute incubation at 37° C. in the presence or absence of NAD+ or NADP followed. Reaction mixtures were then extracted with n-hexane, and organic phases removed and dried under argon. The dried organic phases were then separately dissolved in ethanol and aliquots were analyzed on a normal phase silica HPLC column developed with n-hexane containing 4% dioxane at 1 ml per minute. See Saari et al. J. Biol. Chem. 257:13329–13333 (1982). Effluent was monitored at 330 nm. Under these conditions, 11-cis-retinaldehyde and 11-cis retinol eluted at 7 minutes and 22.5 minutes, respectively, and all-trans-retinaldehyde and all-trans retinol eluted at 8 minutes and 23 minutes, respectively.

Figure 7B:
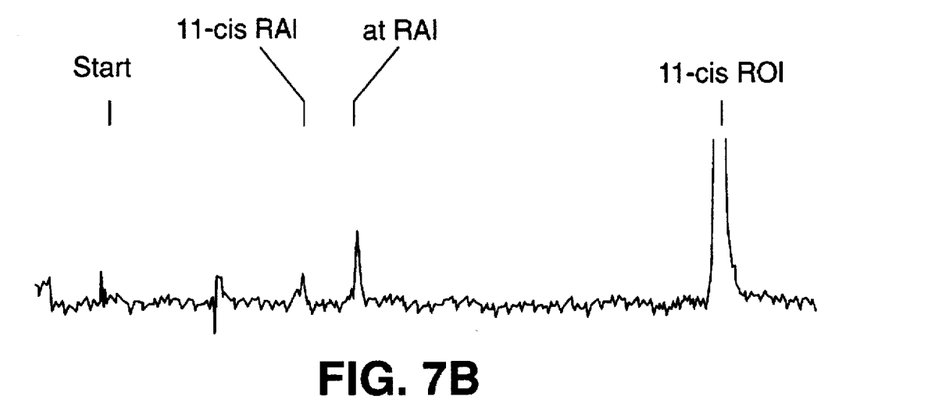
FIG. 7B illustrates the expression of 11-cis retinol dehydrogenase activity in the presence of NAD+ as indicated by the formation of 11-cis retinaldehyde.

As indicated in FIG. 7B, the aforementioned HPLC analysis shows that fractions from transfected cells containing p32 expressed 11-cis-retinol dehydrogenase protein which was active in the presence of NAD+, as indicated by the formation of 11-cis-retinaldehyde. A second peak in the chromatogram is all-trans retinaldehyde; however, control incubations with 11-cis retinaldehyde, in the absence of cellular membranes, show that, under the test procedure employed, a large amount of 11-cis retinaldehyde isomerizes to all-trans retinaldehyde. This indicates that the appearance of all-trans retinaldehyde is due to its generation during the incubation process used and extraction procedures, and is not an enzymatic reaction product. Further, incubations with all-trans retinol with cells containing p32 verify the stereo specificity of the enzyme, as no significant formation of all-trans retinaldehyde is detected.

Figure 7C:
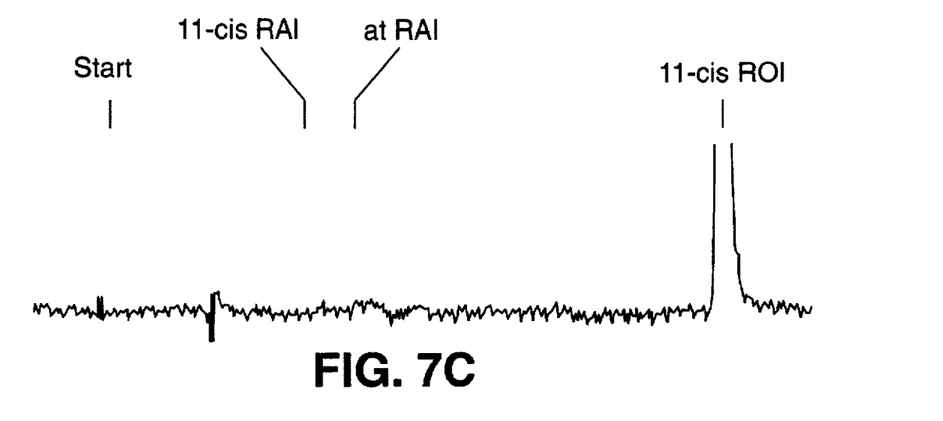
FIG. 7C illustrates the lack of 11-cis-retinol dehydrogenase activity in the presence of cofactor NADP.

As shown in FIG. 7C, p32 is not enzymatically active in the presence of cofactor NADP.

Figure 7D:
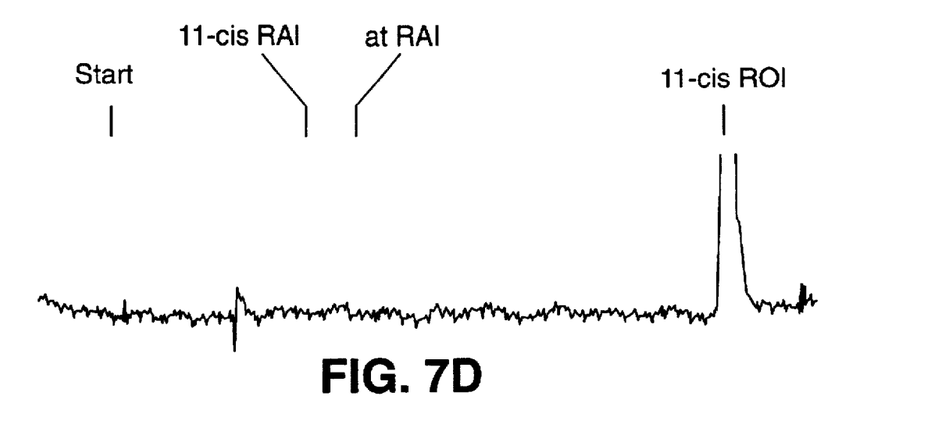
FIG. 7D illustrates control cells not expressing p32 which lack the ability to oxidize 11-cis-retinol into 11-cis-retinaldehyde.

In FIG. 7D, assays of the control cells not expressing p32 show that these do not oxidize 11-cis-retinol into 11-cis-retinaldehyde.

Therefore, the above shows conclusively that p32 is a stereo specific 11-cis-retinol dehydrogenase, which relies on NAD+ as its cofactor.

Thus, one aspect of the invention is the ability to produce recombinant 11-cis-retinal dehydrogenase. The recombinant enzyme can be used to produce 11-cis-retinaldehyde in levels higher, and in purer form, than would be available using standard biochemical methodologies. Thus, the isolated nucleic acid molecules of the invention, which include SEQ ID NO:10, as well as those nucleic acid molecules which hybridize to SEQ ID NO:10 under stringent conditions can be used in this context. By the term "stringent conditions" is meant hybridization in 6×SSC, 0.5% SDS, 5×Denhardt's solution at 68° C., with 100 ug/ml of salmon sperm DNA, and a final wash with 0.5–1.0×SSC at 50° C. The term is also used herein to refer to any set of parameters which are at least as stringent as those set forth above. As is well known, equally stringent conditions can be created by changing one parameter to make it less stringent, with another parameter being changed to increase its stringency. Thus, any nucleic acid molecule which fulfills the hybridization criteria set forth herein will be expected to code for p32 or a p32 homologue. The enzyme may be produced in an in vitro system, such as the one described above, or via transfecting or transforming eukaryotic or prokaryotic cell lines, such as CHO and COS cells or bacterial strains such as E. coli or the yeast strain S.cervisiae with the nucleic acid molecules of the invention. In an especially preferred embodiment, the nucleic acid molecules are contained within an expression vector, operably linked to a promoter. Complementary DNA, or "cDNA" is preferred, but genomic DNA and mRNA can also be used.

The identification of the p32, 11-cis retinol dehydrogenase, as a member of the short-chain alcohol dehydrogenase superfamily is important in view of the retinoid-metabolism which occurs in non-ocular tissues. Studies show that generation of all-trans retinoic acid from all-trans retinol is carried out in a two step process (Posch et al., Biochemistry 30:6224–6230 (1991)). First, retinol is oxidized to retinal by a membrane bound retinol dehydrogenase. In a second step, the retinal is oxidized to retinoic acid. Thus, the oxidation of retinol into retinal, occurring in non-ocular tissues, is similar to the reaction carried out during synthesis of 11-cis retinal from 11-cis retinol in the visual cycle. In light of these similarities, it can be proposed that formation of all-trans retinal from all-trans retinol is carried out by an enzyme which is structurally similar to the p32 11-cis retinol dehydrogenase isolated by this invention.

These findings are surprising in contrast to presently held views as it is generally believed that this metabolic step is carried out by members of the medium chain alcohol dehydrogenases. See Duester, Alcohol Clin. Exp. Res. 15:568–572 (1991); Yang et al., Alcohol Clin. Exp. Res. 17:496 (1993) and Zgombic-Knight et al., J. Biol. Chem. 269:6790–6795 (1994). Thus the identification and structural characterization of the p32 11-cis retinol dehydrogenase, provided by this invention also provides a previously unexpected avenue for the isolation and characterization of similar dehydrogenases involved in retinol metabolism is non-ocular tissues.

The p32 protein and nucleic acid encoding therefor and other aspects of this invention are also useful in many other important applications. For example, as it has been shown that p32 is part of an oligomeric protein complex which functions as a membrane receptor for RBP in RPE-cells, the nucleic acid sequence coding for p32 can be used in a phenotypic/genic diagnostic analysis to determine retinoid accumulation, which can lead to retinitis pigmentosa.

Additionally, as shown, p32 possesses 11-cis-retinol dehydrogenase activity, which catalyzes the conversion of 11-cis retinol to 11-cis-retinaldehyde, a major metabolic step in retinoid metabolism in RPE-cells carried out by a membrane bound dehydrogenase. Thus, retinoid accumulation may be directly or indirectly tied to the presence of p32 and/or its activation or inhibition, for example, its complex formation with the RBP receptor p63.

In other applications the effect of potential retinoid drugs for treatment of various diseases on the 11-cis-retinal dehydrogenase activity of p32 may be assayed as such drugs may adversely effect the enzyme, and to thus determine which of the different drugs have limited or no adverse effect on enzyme activity.

Examples of such diseases include those of the eye and also skin disorders such as psoriasis and acne. Certain cancers such as T-cell leukemias may also be tested by retinoid drugs and hence be candidates for assaying p32 activity.

The various known functions of retinoids also suggests that various other retinoid linked pathological conditions may be diagnosed via assays for levels of the p63/p32 receptor complex associated with a particular retinol binding protein. Art recognized techniques may be used, such a immunoassays, and so forth, to determine whether p63/p32 receptor complex levels are too low or too high—i.e., are at variance with a normal level. Further, as p32 complexes with the p63 component of the retinoid uptake machinery in RPE cells, it may also be used in a therapeutic context, as it is well known that soluble receptors may be used to prevent binding of a protein to its membrane-linked receptor. Thus, a subject characterized by enhanced levels of production of retinol binding protein may be treated via administering an amount of soluble receptor complex or antibody sufficient to inhibit binding of the retinol binding protein or other related molecule to its target, namely, an inhibitor of p32's retinol dehydrogenase activity. Other aspects of the invention will be clear to the skilled artisan and need not be repeated here.

In yet another application, monoclonal and polyclonal antibodies to p32 can be generated, which are useful, inter alia, in monitoring the instance of pathological conditions characterized by aberrant levels of a receptor for retinol binding protein, by binding analysis of the antibody with body fluid or tissue samples. The generation of antibodies to p32 can be accomplished, for example, by using the procedure set out in Bavik et al., J. Biol. Chem. 268:20540–20546 (1993) for the generation of antibodies to p63, including mAb A52.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

---

We claim:

1. An isolated nucleic acid molecule which hybridizes to a nucleic acid molecule having the complement of the nucleotide sequence presented in SEQ ID NO:10, under stringent conditions.

2. The isolated nucleic acid molecule of claim 1, wherein said isolated nucleic acid molecule has the nucleotide sequence set forth in SEQ ID NO:10.

3. The cell line or the bacterial cell strain, transformed or transfected with an expression vector which comprises the isolated nucleic acid molecule of claim 2, operably linked to a promoter.

4. An expression vector comprising the isolated nucleic acid molecule of claim 2, operably linked to a promoter.

5. The isolated nucleic acid molecule of claim 1, wherein said isolated nucleic acid molecule encodes a protein having an amino acid sequence which is encoded by an open reading frame defined by nucleotides 36–989 of SEQ ID NO: 10, wherein said open reading frame begins at nucleotide 36 of SEQ ID NO:10.

6. A cell line or a bacterial cell strain, transformed or transfected with an expression vector which comprises the isolated nucleic acid molecule of claim 5, operably linked to a promoter.

7. The cell line or the bacterial cell strain, transformed or transfected with the isolated nucleic acid molecule of claim 5 operably linked to a promoter.

8. An expression vector comprising the isolated nucleic acid molecule of claim 5, operably linked to a promoter.

9. An expression vector comprising the isolated nucleic acid molecule of claim 5, operably linked to a promoter.

10. An isolated nucleic acid molecule selected from the group consisting of (i) a nucleic acid molecule having the nucleotide sequence presented by SEQ ID NO:6, (ii) a nucleic acid molecule having the nucleotide sequence presented by SEQ ID NO:7, (iii) a nucleic acid molecule having the nucleotide sequence represented by SEQ ID NO:8, and (iv) a nucleic acid molecule having the nucleotide sequence presented by SEQ ID NO:9.

* * * * *

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO: 1:

Leu Val Glu Ala Val Leu Ala Glu Val Leu Pro Lys Pro Ala Gln Thr
              5                      10                 15

Val Ala ( 2 ) INFORMATION FOR SEQ ID NO: 2:

( i ) SEQUENCE CHARACTERISTICS:
        ( A ) LENGTH: 8 amino acids
        ( B ) TYPE: amino acid
        ( C ) STRANDEDNESS: single ( D ) TOPOLOGY: linear ( i i ) MOLECULE TYPE: protein ( x i ) SEQUENCE DESCRIPTION: SEQ ID NO: 2:

Tyr Ser Pro Gly Trp Asp Ala Lys
                     5

( 2 ) INFORMATION FOR SEQ ID NO: 3:

( i ) SEQUENCE CHARACTERISTICS:
            ( A ) LENGTH: 15 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO: 3:

Thr Pro Val Thr Asn Leu Glu Thr Leu Glu Asp Thr Leu Gln Ala
                 5                   10                  15

( 2 ) INFORMATION FOR SEQ ID NO: 4:

( i ) SEQUENCE CHARACTERISTICS:
            ( A ) LENGTH: 7 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO: 4:

Asp Val Ala Pro Phe Gly Val
                 5

( 2 ) INFORMATION FOR SEQ ID NO: 5:

( i ) SEQUENCE CHARACTERISTICS:
            ( A ) LENGTH: 14 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO: 5:

Leu His Thr Thr Leu Leu Asp Val Thr Asp Pro Gln Ser Ile
                 5                   10

( 2 ) INFORMATION FOR SEQ ID NO: 6:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: nucleic acid ( x i ) SEQUENCE DESCRIPTION: SEQ ID NO: 6:

ACGTGAATTC TNGTNGARGC NGT                                                    2 3

( 2 ) INFORMATION FOR SEQ ID NO: 7:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i i ) MOLECULE TYPE: nucleic acid ( x i ) SEQUENCE DESCRIPTION: SEQ ID NO: 7:

ACGTGAATTC ACNGT Y TGNG CNGG Y TT                    27

( 2 ) INFORMATION FOR SEQ ID NO: 8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: nucleic acid     ( x i ) SEQUENCE DESCRIPTION: SEQ ID NO: 8:

ACGTGAATTC CCNGTNACNA A Y YT                         24

( 2 ) INFORMATION FOR SEQ ID NO: 9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( i i ) MOLECULE TYPE: nucleic acid     ( x i ) SEQUENCE DESCRIPTION: SEQ ID NO: 9:

ACGTGAATTC GC Y TGNARNG TRTC Y TC                    27

( 2 ) INFORMATION FOR SEQ ID NO: 10:

( i ) SEQUENCE CHARACTERISTICS:
        ( A ) LENGTH: 1122 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: p32;11-cis retinol dehydrogenase     ( x i ) SEQUENCE DESCRIPTION: SEQ ID NO:10:

```
AGCTTTCCCC TGAGGAGGTC ACCTGGGCTC CAGCC ATG TGG CTG CCT CTG CAG    53
                                      Met Trp Leu Pro Leu Leu
                                                        5

TGC CTG CTG CTG GGT GTC TTG CTC TGG GCA GCA CTG TGG TTG CTC AGG  101
Leu Gly Val Leu Leu Trp Ala Ala Leu Trp Leu Leu Arg Asp Arg Gln
             10              15                      20

GAC CGG CCA GCC AGC GAT GCC TTT ATC TTC ATC ACC GGC TGT GAC TCG  149
Cys Leu Pro Ala Ser Asp Ala Phe Ile Phe Ile Thr Gly Cys Asp Ser
         25                  30                  35

GGC TTT GGG CGG CTC CTT GCT CTG AGG CTG GAC CAG AGA GGC TTC CGA  197
Gly Phe Gly Arg Leu Leu Ala Leu Arg Leu Asp Gln Arg Gly Phe Arg
     40                  45                  50

GTA CTG GCC AGC TGC CTG ACA CCC TCG GGG GCG GAG GAC CTC CAG CGG  245
Val Leu Ala Ser Cys Leu Thr Pro Ser Gly Ala Glu Asp Leu Gln Arg
55                  60                  65                  70

GTC GCC TCC TCC CGC CTC CAC ACC ACC CTG CTG GAT GTC ACA GAT CCC  293
Val Ala Ser Ser Arg Leu His Thr Thr Leu Leu Asp Val Thr Asp Pro
                 75              80                  85

CAG AGC ATC CGG CAG GCA GTC AAG TGG GTG GAA ACG CAT GTT GGG GAA  341
   Gln Ser Ile Arg Gln Ala Val Lys Trp Val Glu Thr His Val Gly Glu
                90                  95                  100
```

```
GCA GGG CTT TTT GGT CTG GTG AAT AAT GCT GGT GTG GCT GGC ATC ATT   389
Ala Gly Leu Phe Gly Leu Val Asn Asn Ala Gly Val Ala Gly Ile Ile
        105                 110                 115

GGT CCC ACC CCA TGG CAG ACG CGG GAG GAC TTC CAG CGG GTG CTG AAT   437
Gly Pro Thr Pro Trp Gln Thr Arg Glu Asp Phe Gln Arg Val Leu Asn
    120                 125                 130

GTG AAC ACG CTG GGT CCC ATC GGG GTC ACC CTC GCC CTG CTG CCC CTG   485
Val Asn Thr Leu Gly Pro Ile Gly Val Thr Leu Ala Leu Leu Pro Leu
135                 140                 145                 150

CTG CTG CAG GCC CGG GGC CGA GTG ATC AAC ATC ACC AGT GTC CTT GGC   533
Leu Leu Gln Ala Arg Gly Arg Val Ile Asn Ile Thr Ser Val Leu Gly
                155                 160                 165

CGT CTG GCA GCC AAT GGA GGG GGC TAC TGC GTC TCC AAG TTT GGC CTG   581
Arg Leu Ala Ala Asn Gly Gly Gly Tyr Cys Val Ser Lys Phe Gly Leu
            170                 175                 180

GAG GCC TTC TCT GAC AGC CTG AGG CGA GAT GTG GCT CCT TTT GGG GTA   629
Glu Ala Phe Ser Asp Ser Leu Arg Arg Asp Val Ala Pro Phe Gly Val
                185                 190                 195

CGG GTC TCT ATC GTG GAA CCT GGC TTC TTC CGA ACC CCT GTG ACA AAC   677
Arg Val Ser Ile Val Glu Pro Gly Phe Phe Arg Thr Pro Val Thr Asn
        200                 205                 210

CTG GAA ACT TTG GAG GAC ACC CTG CAG GCC TGC TGG GCA CGG CTG CCT   725
Leu Glu Thr Leu Glu Asp Thr Leu Gln Ala Cys Trp Ala Arg Leu Pro
215                 220                 225                 230

CCA GCC ACA CAG GCC CTC TAT GGG GAG GCC TTC CTC ACC AAA TAC CTG   773
Pro Ala Thr Gln Ala Leu Tyr Gly Glu Ala Phe Leu Thr Lys Tyr Leu
                235                 240                 245

AGA GTG CAG CAA CGT ATC ATG AAC ATG ATC TGT GAT CCG GAC CTG GCC   821
Arg Val Gln Gln Arg Ile Met Asn Met Ile Cys Asp Pro Asp Leu Ala
            250                 255                 260

AAG GTG AGC AGG TGC CTG GAG CAT GCC CTA ACT GCC CGT CAC CCC AGA   869
Lys Val Ser Arg Cys Leu Glu His Ala Leu Thr Ala Arg His Pro Arg
        265                 270                 275

ACC CGC TAC AGC CCA GGC TGG GAT GCC AAG CTC CTC TGG TTG CCA GCC   917
Thr Arg Tyr Ser Pro Gly Trp Asp Ala Lys Leu Leu Trp Leu Pro Ala
    280                 285                 290

TCC TAC TTG CCA GCC AGG CTG GTG GAT GCT GTG CTC GCC TGG GTC CTT   965
Ser Tyr Leu Pro Ala Arg Leu Val Asp Ala Val Leu Ala Trp Val Leu
295                 300                 305                 310

CCC AAG CCT GCC CAG ACA GTC TAC TAA ATCCAGCCCT CCAGCAAAAG        1012
Pro Lys Pro Ala Gln Thr Val Tyr
                315

ATGGTTGTTC AAGGCAAGGA CTCTGATTTA TTCTGTCCCC TACCCTGGTA          1062

CTGCCTGGTG TGTGGCATAA AACAGTCACT CAATAAATGT ATTATTCAAA          1112

ACAAAAAAAA                                                      1122
```

( 2 ) INFORMATION FOR SEQ ID NO: 11:

( i ) SEQUENCE CHARACTERISTICS:
        ( A ) LENGTH: 344 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Rat D-b- hydroxybutyrate dehydrogenase
           ( r BDH )

( x i ) SEQUENCE DESCRIPTION: SEQ ID NO:11:

-continued

| | | | | | | | | | | | | | | |
|---|---|---|---|---|---|---|---|---|---|---|---|---|---|---|
| Met | Met | Leu | Ala | Ala<br>5 | Arg | Leu | Ser | Arg | Pro<br>10 | Leu | Ser | Gln | Leu | Pro<br>15 | Gly |
| Lys | Ala | Leu | Ser<br>20 | Val | Cys | Asp | Arg | Glu<br>25 | Asn | Gly | Thr | Arg | His<br>30 | Thr | Leu |
| Leu | Phe | Tyr<br>35 | Pro | Ala | Ser | Phe | Ser<br>40 | Pro | Asp | Thr | Arg | Arg<br>45 | Thr | Tyr | Thr |
| Ser | Gln<br>50 | Ala | Asp | Ala | Ala | Ser<br>55 | Gly | Lys | Ala | Val | Leu<br>60 | Val | Thr | Gly | Cys |
| Asp<br>65 | Ser | Gly | Phe | Gly | Phe<br>70 | Ser | Leu | Ala | Lys | His<br>75 | Leu | His | Ser | Lys | Gly<br>80 |
| Phe | Leu | Val | Phe | Ala<br>85 | Gly | Cys | Leu | Leu | Lys<br>90 | Glu | Gln | Gly | Asp | Ala<br>95 | Gly |
| Val | Arg | Glu | Leu<br>100 | Asp | Ser | Leu | Lys | Ser<br>105 | Asp | Arg | Leu | Arg | Thr<br>110 | Ile | Gln |
| Leu | Asn | Val<br>115 | Cys | Asn | Ser | Glu | Glu<br>120 | Val | Glu | Lys | Ala | Val<br>125 | Glu | Thr | Val |
| Arg | Ser<br>130 | Gly | Leu | Lys | Asp | Pro<br>135 | Glu | Lys | Gly | Met | Trp<br>140 | Gly | Leu | Val | Asn |
| Asn<br>145 | Ala | Gly | Ile | Ser | Thr<br>150 | Phe | Gly | Glu | Val | Glu<br>155 | Phe | Thr | Ser | Met | Glu<br>160 |
| Thr | Tyr | Lys | Glu | Val<br>165 | Ala | Glu | Val | Asn | Leu<br>170 | Trp | Gly | Thr | Val | Arg<br>175 | Thr |
| Thr | Lys | Ser | Phe<br>180 | Leu | Pro | Leu | Leu | Arg<br>185 | Arg | Ala | Lys | Gly | Arg<br>190 | Val | Val |
| Asn | Ile | Ser<br>195 | Ser | Met | Leu | Gly | Arg<br>200 | Met | Ala | Asn | Pro | Ala<br>205 | Arg | Ser | Pro |
| Tyr | Cys<br>210 | Ile | Thr | Lys | Phe | Gly<br>215 | Val | Glu | Ala | Phe | Ser<br>220 | Asp | Cys | Leu | Arg |
| Tyr<br>225 | Glu | Met | His | Pro | Leu<br>230 | Gly | Val | Lys | Val | Ser<br>235 | Val | Val | Glu | Pro | Gly<br>240 |
| Asn | Phe | Ile | Ala | Ala<br>245 | Thr | Ser | Leu | Tyr | Ser<br>250 | Pro | Glu | Arg | Ile | Gln<br>255 | Ala |
| Ile | Ala | Lys | Lys<br>260 | Met | Trp | Asp | Glu | Leu<br>265 | Pro | Glu | Val | Val | Arg<br>270 | Lys | Asp |
| Tyr | Gly | Lys<br>275 | Lys | Tyr | Phe | Asp | Glu<br>280 | Lys | Ile | Ala | Lys | Met<br>285 | Glu | Thr | Tyr |
| Cys | Asn<br>290 | Ser | Gly | Ser | Thr | Asp<br>295 | Thr | Ser | Ser | Val | Ile<br>300 | Asn | Ala | Val | Thr |
| His<br>305 | Ala | Leu | Thr | Ala | Ala<br>310 | Thr | Pro | Tyr | Thr | Arg<br>315 | Tyr | His | Pro | Met | Asp<br>320 |
| Tyr | Tyr | Trp | Trp | Leu<br>325 | Arg | Met | Gln | Val | Met<br>330 | Thr | His | Phe | Pro | Gly<br>335 | Ala |
| Ile | Ser | Asp | Lys<br>340 | Ile | Tyr | Ile | His | | | | | | | | |

( 2 ) INFORMATION FOR SEQ ID NO: 12:

( i ) SEQUENCE CHARACTERISTICS:
        ( A ) LENGTH: 327 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Human estradiol 17-b dehydrogenase (hEDH)

( x i ) SEQUENCE DESCRIPTION: SEQ ID NO:12:

| | | | | | | | | | | | | | | | |
|---|---|---|---|---|---|---|---|---|---|---|---|---|---|---|---|
| Ala | Arg | Thr | Val | Val<br>5 | Leu | Ile | Thr | Gly<br>10 | Cys | Ser | Ser | Gly | Ile | Gly<br>15 | Leu |
| His | Leu | Ala | Val<br>20 | Arg | Leu | Ala | Ser | Asp<br>25 | Pro | Ser | Gln | Ser | Phe<br>30 | Lys | Val |
| Tyr | Ala | Thr<br>35 | Leu | Arg | Asp | Leu | Lys<br>40 | Thr | Gln | Gly | Arg | Leu<br>45 | Trp | Glu | Ala |
| Ala | Arg<br>50 | Ala | Leu | Ala | Cys | Pro<br>55 | Pro | Gly | Ser | Leu | Glu<br>60 | Thr | Leu | Gln | Leu |
| Asp<br>65 | Val | Arg | Asp | Ser | Lys<br>70 | Ser | Val | Ala | Ala | Ala<br>75 | Arg | Glu | Arg | Val | Thr<br>80 |
| Glu | Gly | Arg | Val | Asp<br>85 | Val | Leu | Val | Cys | Asn<br>90 | Ala | Gly | Leu | Gly | Leu<br>95 | Leu |
| Gly | Pro | Leu | Glu<br>100 | Ala | Leu | Gly | Glu | Asp<br>105 | Ala | Val | Ala | Ser | Val<br>110 | Leu | Asp |
| Val | Asn | Val<br>115 | Val | Gly | Thr | Val | Arg<br>120 | Met | Leu | Gln | Ala | Phe<br>125 | Leu | Pro | Asp |
| Met | Lys<br>130 | Arg | Arg | Gly | Ser | Gly<br>135 | Arg | Val | Leu | Val | Thr<br>140 | Gly | Ser | Val | Gly |
| Gly<br>145 | Leu | Met | Gly | Leu | Pro<br>150 | Phe | Asn | Asp | Val | Tyr<br>155 | Cys | Ala | Ser | Lys | Phe<br>160 |
| Ala | Leu | Glu | Gly | Leu<br>165 | Cys | Glu | Ser | Leu | Ala<br>170 | Val | Leu | Leu | Leu | Pro<br>175 | Phe |
| Gly | Val | His | Leu<br>180 | Ser | Leu | Ile | Glu | Cys<br>185 | Gly | Pro | Val | His | Thr<br>190 | Ala | Phe |
| Met | Glu | Lys<br>195 | Val | Leu | Gly | Ser | Pro<br>200 | Glu | Glu | Val | Leu | Asp<br>205 | Arg | Thr | Asp |
| Ile | His<br>210 | Thr | Phe | His | Arg | Phe<br>215 | Tyr | Gln | Tyr | Leu | Ala<br>220 | His | Ser | Lys | Gln |
| Val<br>225 | Phe | Arg | Glu | Ala | Ala<br>230 | Gln | Asn | Pro | Glu | Glu<br>235 | Val | Ala | Glu | Val | Phe<br>240 |
| Leu | Thr | Ala | Leu | Arg<br>245 | Ala | Pro | Lys | Pro | Thr<br>250 | Leu | Arg | Tyr | Phe | Thr<br>255 | Thr |
| Glu | Arg | Phe | Leu<br>260 | Pro | Leu | Leu | Arg | Met<br>265 | Arg | Leu | Asp | Asp | Pro<br>270 | Ser | Gly |
| Ser | Asn | Tyr<br>275 | Val | Thr | Ala | Met | His<br>280 | Arg | Glu | Val | Phe | Gly<br>285 | Asp | Val | Pro |
| Ala | Lys<br>290 | Ala | Glu | Ala | Gly | Ala<br>295 | Glu | Ala | Gly | Gly | Gly<br>300 | Ala | Gly | Pro | Gly |
| Ala<br>305 | Glu | Asp | Glu | Ala | Gly<br>310 | Arg | Ser | Ala | Val | Gly<br>315 | Asp | Pro | Glu | Leu | Gly<br>320 |
| Asp | Pro | Pro | Ala | Ala<br>325 | Pro | Gln | | | | | | | | | |

( 2 ) INFORMATION FOR SEQ ID NO: 13:

( i ) SEQUENCE CHARACTERISTICS:
        ( A ) LENGTH: 244 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY:E.coli 3-oxoacyl[acyl carrier protein]
            reductase (FABG)

( x i ) SEQUENCE DESCRIPTION: SEQ ID NO:13:

| Met | Asn | Phe | Glu | Gly | Lys | Ile | Ala | Leu | Val | Thr | Gly | Ala | Ser | Arg | Gly |
|---|---|---|---|---|---|---|---|---|---|---|---|---|---|---|---|
| | | | | 5 | | | | 10 | | | | | | 15 | |

| Ile | Gly | Arg | Ala | Ile | Ala | Glu | Thr | Leu | Ala | Ala | Arg | Gly | Gly | Lys | Val |
|---|---|---|---|---|---|---|---|---|---|---|---|---|---|---|---|
| | | | 20 | | | | | 25 | | | | | 30 | | |

| Ile | Gly | Thr | Ala | Thr | Ser | Glu | Asn | Gly | Ala | Gln | Ala | Ile | Ser | Asp | Tyr |
| | | 35 | | | | | 40 | | | | | 45 | | | |

| Leu | Gly | Ala | Asn | Gly | Lys | Gly | Leu | Met | Leu | Asn | Val | Thr | Asp | Pro | Ala |
| | 50 | | | | | 55 | | | | | 60 | | | | |

| Ser | Ile | Glu | Ser | Val | Leu | Glu | Lys | Ile | Arg | Ala | Glu | Phe | Gly | Glu | Val |
| 65 | | | | | 70 | | | | | 75 | | | | | 80 |

| Asp | Ile | Leu | Val | Asn | Asn | Ala | Gly | Ile | Thr | Arg | Asp | Asn | Leu | Leu | Met |
| | | | | 85 | | | | | 90 | | | | | 95 | |

| Arg | Met | Lys | Asp | Glu | Glu | Trp | Asn | Asp | Ile | Ile | Glu | Thr | Asn | Leu | Ser |
| | | | 100 | | | | | 105 | | | | | 110 | | |

| Ser | Val | Phe | Arg | Leu | Ser | Lys | Ala | Val | Met | Arg | Ala | Met | Met | Lys | Lys |
| | | 115 | | | | | 120 | | | | | 125 | | | |

| Arg | His | Gly | Arg | Ile | Ile | Thr | Ile | Gly | Ser | Val | Val | Gly | Thr | Met | Gly |
| | 130 | | | | | 135 | | | | | 140 | | | | |

| Asn | Gly | Gly | Gln | Ala | Asn | Tyr | Ala | Ala | Ala | Lys | Ala | Gly | Leu | Ile | Gly |
| 145 | | | | | 150 | | | | | 155 | | | | | 160 |

| Phe | Ser | Lys | Ser | Leu | Ala | Arg | Glu | Val | Ala | Ser | Arg | Gly | Ile | Thr | Val |
| | | | | 165 | | | | | 170 | | | | | 175 | |

| Asn | Val | Val | Ala | Pro | Gly | Phe | Ile | Glu | Thr | Asp | Met | Thr | Arg | Ala | Leu |
| | | | 180 | | | | | 185 | | | | | 190 | | |

| Ser | Asp | Asp | Gln | Arg | Ala | Gly | Ile | Leu | Ala | Gln | Val | Pro | Ala | Gly | Arg |
| | | 195 | | | | | 200 | | | | | 205 | | | |

| Leu | Gly | Gly | Ala | Gln | Glu | Ile | Ala | Asn | Ala | Val | Ala | Phe | Leu | Ala | Ser |
| | 210 | | | | | 215 | | | | | 220 | | | | |

| Asp | Glu | Ala | Ala | Tyr | Ile | Thr | Gly | Glu | Thr | Leu | His | Val | Asn | Gly | Gly |
| 225 | | | | | 230 | | | | | 235 | | | | | 240 |

| Met | Tyr | Met | Val |
|---|---|---|---|

( 2 ) INFORMATION FOR SEQ ID NO: 14:

( i ) SEQUENCE CHARACTERISTICS:
        ( A ) LENGTH: 318 amino acids
        ( B ) TYPE: amino acid
        ( D ) TOPOLOGY: linear     ( i i ) MOLECULE TYPE: amino acid     ( i x ) FEATURE:
        ( A ) NAME/KEY: p32;11-cis retinol dehydrogenase ( x i ) SEQUENCE DESCRIPTION: SEQ ID NO:14:

| | | | | | | | | | | Met | Trp | Leu | Pro | Leu | Leu |
|---|---|---|---|---|---|---|---|---|---|---|---|---|---|---|---|
| | | | | | | | | | | | | | | 5 | |

| Leu | Gly | Val | Leu | Leu | Trp | Ala | Ala | Leu | Trp | Leu | Leu | Arg | Asp | Arg | Gln |
| | | | 10 | | | | | 15 | | | | | 20 | | |

| Cys | Leu | Pro | Ala | Ser | Asp | Ala | Phe | Ile | Phe | Ile | Thr | Gly | Cys | Asp | Ser |
| | | 25 | | | | | 30 | | | | | 35 | | | |

| Gly | Phe | Gly | Arg | Leu | Leu | Ala | Leu | Arg | Leu | Asp | Gln | Arg | Gly | Phe | Arg |
| | 40 | | | | | 45 | | | | | 50 | | | | |

| Val | Leu | Ala | Ser | Cys | Leu | Thr | Pro | Ser | Gly | Ala | Glu | Asp | Leu | Gln | Arg |
| 55 | | | | | 60 | | | | | 65 | | | | | 70 |

| Val | Ala | Ser | Ser | Arg | Leu | His | Thr | Thr | Leu | Leu | Asp | Val | Thr | Asp | Pro |

```
                        75                        80                              85

Gln Ser Ile Arg Gln Ala Val Lys Trp Val Glu Thr His Val Gly Glu
            90              95                      100
Ala Gly Leu Phe Gly Leu Val Asn Asn Ala Gly Val Ala Gly Ile Ile
            105             110                 115
Gly Pro Thr Pro Trp Gln Thr Arg Glu Asp Phe Gln Arg Val Leu Asn
    120             125                 130
Val Asn Thr Leu Gly Pro Ile Gly Val Thr Leu Ala Leu Leu Pro Leu
135             140                 145                         150
Leu Leu Gln Ala Arg Gly Arg Val Ile Asn Ile Thr Ser Val Leu Gly
                155             160                     165
Arg Leu Ala Ala Asn Gly Gly Gly Tyr Cys Val Ser Lys Phe Gly Leu
            170             175                 180
Glu Ala Phe Ser Asp Ser Leu Arg Arg Asp Val Ala Pro Phe Gly Val
        185             190                 195
Arg Val Ser Ile Val Glu Pro Gly Phe Phe Arg Thr Pro Val Thr Asn
    200             205                 210
Leu Glu Thr Leu Glu Asp Thr Leu Gln Ala Cys Trp Ala Arg Leu Pro
215             220                 225                         230
Pro Ala Thr Gln Ala Leu Tyr Gly Glu Ala Phe Leu Thr Lys Tyr Leu
            235                 240                     245
Arg Val Gln Gln Arg Ile Met Asn Met Ile Cys Asp Pro Asp Leu Ala
            250             255                     260
Lys Val Ser Arg Cys Leu Glu His Ala Leu Thr Ala Arg His Pro Arg
        265             270                 275
Thr Arg Tyr Ser Pro Gly Trp Asp Ala Lys Leu Leu Trp Leu Pro Ala
    280             285                 290
Ser Tyr Leu Pro Ala Arg Leu Val Asp Ala Val Leu Ala Trp Val Leu
295             300                 305                         310
Pro Lys Pro Ala Gln Thr Val Tyr
                315
```